US00PP26811P3

(12) United States Plant Patent
Pavlich

(10) Patent No.: US PP26,811 P3
(45) Date of Patent: Jun. 7, 2016

(54) ***BEGONIA* PLANT NAMED 'ST. NICK'**

(50) Latin Name: *Begonia rex-cultorum*
Varietal Denomination: St. Nick

(71) Applicant: Terra Nova Nurseries, Inc., Canby, OR (US)

(72) Inventor: John C. Pavlich, East Olympia, WA (US)

(73) Assignee: Terra Nova Nurseries, Inc., Canby, OR (US)

( * ) Notice: Subject to any disclaimer, the term of this patent is extended or adjusted under 35 U.S.C. 154(b) by 109 days.

(21) Appl. No.: 14/121,784

(22) Filed: Oct. 17, 2014

(65) Prior Publication Data

US 2016/0113181 P1 Apr. 21, 2016

(51) Int. Cl.
*A01H 5/02* (2006.01)

(52) U.S. Cl.
USPC ..... Plt./343

(58) Field of Classification Search
USPC ..... Plt./343
See application file for complete search history.

*Primary Examiner* — Susan McCormick Ewoldt
(74) *Attorney, Agent, or Firm* — Klarquist Sparkman, LLP

(57) ABSTRACT

A new and distinct form of *Begonia* plant characterized by leaves with a starry red center surrounded by emerald green with white polka dots, a dense, bushy habit, medium pink flowers in summer and fall, and excellent vigor.

1 Drawing Sheet

Botanical denomination: *Begonia rex-cultorum.*
Variety designation: 'St. Nick'.

BACKGROUND

The present invention relates to a new and distinct cultivar of *Begonia,* of the family Begoniaceae, and given the cultivar name, 'St. Nick'. The new cultivar originated from a cross between a proprietary, unreleased rhizomatous *Begonia* seedling, as the seed parent, and an unnamed *Begonia rex-cultorum* seedling, as the pollen parent. This selection is uniquely characterized by:

1. Leaves with a starry red center surrounded by emerald green with white polka dots,
2. a dense, bushy habit,
3. medium pink flowers in summer and fall, and
4. excellent vigor.

Compared to the seed parent, a proprietary, unreleased rhizomatous *Begonia* seedling, the new cultivar has a different leaf shape and has a strongly spiral sinus and displays a spattered color pattern rather than defined, straight colors.

Compared to the pollen parent, an unnamed *Begonia rex-cultorum* seedling the new cultivar has a different leaf shape and displays a spattered color pattern rather than a solid red color.

Compared to *Begonia* 'Painter's Palette', U.S. Plant Pat. No. 25,017, the new cultivar has a different pattern and a spiral sinus and is a smaller plant overall.

The new variety has been reproduced only by asexual propagation (leaf cuttings and tissue culture). Each of the progeny exhibits identical characteristics to the original plant. Asexual propagation by micropropagation as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows a close up of the flowers and leaf of *Begonia* 'St. Nick'.

FIG. 2 shows a 9 month old plant in a growing in a one gallon container in late June in Canby. Oreg.

DETAILED PLANT DESCRIPTION

The following is a detailed description of the new *Begonia* cultivar based on observations of four month-old specimens grown outside in one gallon containers in shade in early September in Canby, Oreg. Canby is Zone 8 on the USDA Hardiness map. Temperatures range from a high of 95° F. in August to 32° F. in January. Normal rainfall in Canby is 42.8 inches per year. The color descriptions are all based on *The Royal Horticultural Society Colour Chart,* 5$^{th}$ edition, 2007.

Plant:

*Type.*—Herbaceous rhizomatous perennial.
*Form.*—Clumping, caulescent.
*Cold hardiness.*—USDA Zone 10a.
*Size.*—Grows to 36 cm tall and 65 cm wide.
*Vigor.*—Excellent.
*Roots and rooting.*—Roots appear on leaf cuttings in 2 weeks; fine, fibrous, and white in color.

Stem:

*Type.*—Upright, congested.
*Size.*—Grows to 5 cm long and 20 mm wide.
*# stems from base.*—17.
*Lateral branches.*—None.
*Internodes.*—About 0.5 cm long.
*Surface.*—Pubescent.
*Color.*—Greyed Red 177A.

Leaf:

*Type.*—Simple.
*Arrangement.*—Alternate, congested.

*Number.*—About 50.

*Shape.*—Obliquely broadly ovate or orbicular.

*Margins.*—Coarsely serrate and shallowly palmately lobed.

*Apex.*—Acute to acuminate.

*Base.*—Oblique and spiral.

*Venation.*—Palmate, Brown 200B on topside, bottom side Greyed Purple 183B.

*Blade size.*—Grows to 24 cm wide and 16 cm long.

*Surface texture.*—Sparsely pubescent on top and bottom.

*Leaf strength.*—Excellent, tough, somewhat brittle.

*Stipules.*—Deciduous, triangular, 18 mm long and 13 mm wide, apex caudate, base clasping, margin entire, topside glabrous, bottom side pubescent, both sides Greyed Purple 183D.

*Petiole description.*—Grows to 28.5 cm long and 9 mm wide, succulent, pubescent, Brown 200C.

*Leaf color.*—Top side from petiole out — Greyed Purple N186A along veins to Red Purple 60B in a star pattern to Green 136A with large spots (2 mm to 7 mm wide) of White NN155C, most with small dots of Red Purple 60B in the center to leaf margins of Greyed Purple N186A; bottom side Greyed Purple 187A along veins lightening to Greyed Green 191A tinted with Greyed Purple 187A.

Inflorescence:

*Type.*—Axillary, bisexual, cyme to compound cyme.

*Number of flowers per cyme.*—3 to 10.

*Peduncle description.*—Grows 21.4 cm long and 7 mm wide, pubescent, fleshy, Greyed Orange 165A; with 2 opposite, dehiscent petiolate leaf-bracts below each cyme, cupped, oblong, 6 mm wide and 8 mm long, margins entire, tip apiculate, back side pubescent, inside glabrous, both sides Greyed Orange 166D.

*Pedicel description.*—Grow to 5 cm long, 1.5 mm wide, fleshy, glabrous, Red 54A.

*Bloom period.*—Early winter in Canby, Oreg.

Flower bud:

*Size.*—Staminate flowers 15 mm long and 14 mm wide prior to opening; pistillate flowers are 10 mm deep and 7 mm wide prior to opening.

*Shape.*—Teardrop.

*Surface texture.*—Pubescent.

*Color.*—Red Purple 61B.

Flower:

*Type.*—Monoecious, bilaterally symmetrical.

*Pistillate flower.*—Cupped, grows to 28 mm deep and 40 mm wide overall; 5 fleshy tepals, grow to 18 mm long and 11 mm wide, oblong, tip and base obtuse, margins entire, glabrous inside, pubescent outside, Red Purple 63C inside and 63B outside; pistil 1, 20 mm long, ovary to 23 mm wide and 15 mm deep, three winged, two equal and one longer, ovary Red 49C, wings Red 48A, style 1 mm long at base and Red 48A spreading like an Elizabethan color 5 mm deep and 9 mm wide, Red 48A, stigma convolute, Yellow 19B.

*Staminate flower.*—10 mm deep and 42 mm wide, 4 tepals, Red Purple 63C inside and 63B outside, cupped, margin entire, glabrous inside, pubescent outside, tip and base obtuse, oblong, tip and base obtuse, margins entire, glabrous inside, pubescent outside; 2 larger outer tepals 22 mm long and 20 mm wide, broadly ovate, inner tepals grow to 20 mm long and 9 mm wide, elliptic.

*Fragrance.*—None.

*Lastingness.*—A cyme blooms for about 4 weeks on the plant, flowers are self-cleaning.

Fruit and seed: None, sterile.

Diseases and pests: The new cultivar is typical to the genus. No known resistances to pests or diseases. No problems have been found in Canby, Oreg.

I claim:

1. A new and distinct form of *Begonia* plant as hereby illustrated and described.

* * * * *

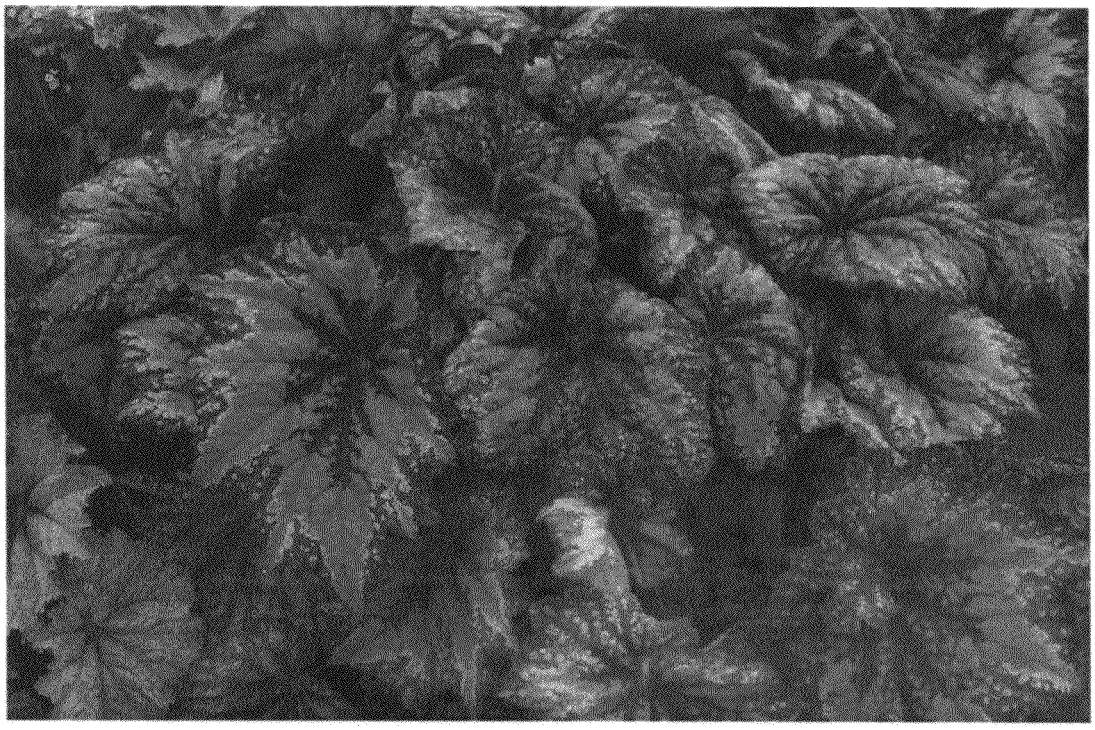

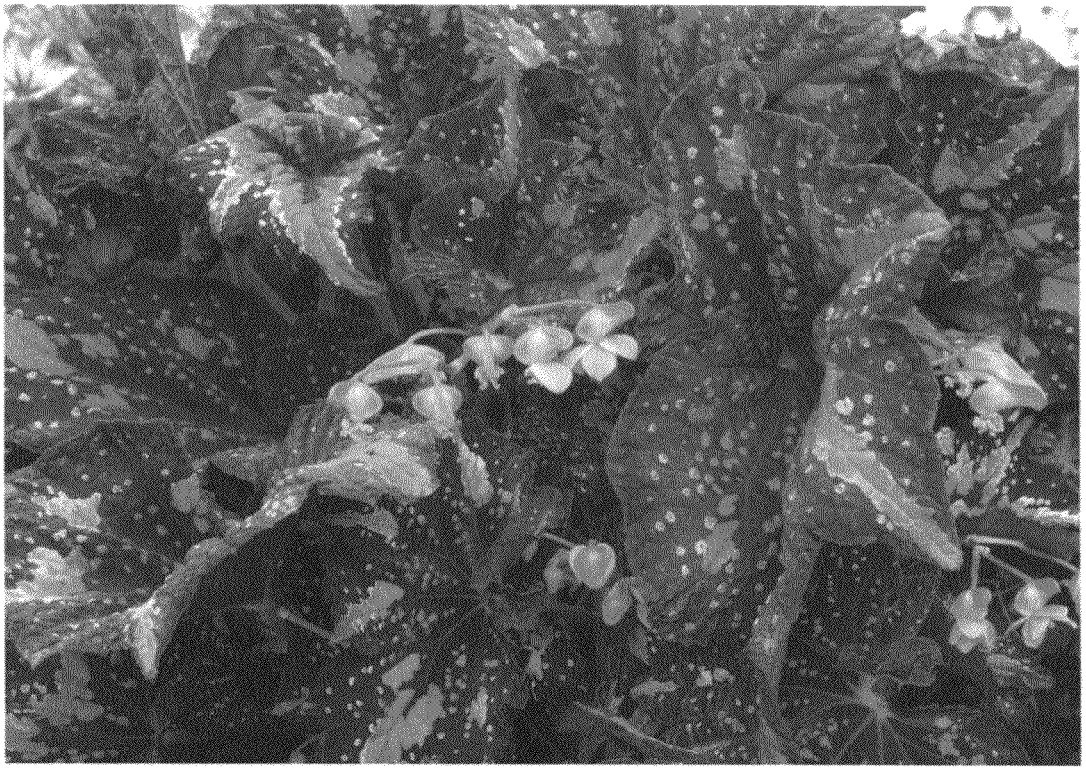
FIG. 1 above, FIG. 2 below